(12) United States Patent
Hogg

(10) Patent No.: US 6,524,265 B2
(45) Date of Patent: Feb. 25, 2003

(54) LEG BRACE SUPPORT STRUCTURE

(76) Inventor: Theodore B. Hogg, 2320 Sans Souci Dr., Aurora, IL (US) 60506

( * ) Notice: Subject to any disclaimer, the term of this patent is extended or adjusted under 35 U.S.C. 154(b) by 0 days.

(21) Appl. No.: 09/844,618

(22) Filed: Apr. 27, 2001

(65) Prior Publication Data

US 2002/0161320 A1 Oct. 31, 2002

(51) Int. Cl.[7] .................................................. A61F 5/00
(52) U.S. Cl. ............................................ 602/23; 602/16
(58) Field of Search ................................ 602/5, 16, 23, 602/26, 27; 128/882; 623/27–29, 39, 47; 2/22

(56) References Cited

U.S. PATENT DOCUMENTS

| | | | |
|---|---|---|---|
| 3,732,862 A | * | 5/1973 | Golia .......................... 602/23 |
| 3,805,773 A | * | 4/1974 | Sichau ........................ 602/27 |
| 3,827,431 A | | 8/1974 | Pecorella |
| 3,844,279 A | | 10/1974 | Konvalin |
| 4,136,404 A | | 1/1979 | Lange |
| 4,463,752 A | | 8/1984 | Liao |
| 4,494,534 A | * | 1/1985 | Hutson ........................ 602/23 |
| 4,688,559 A | | 8/1987 | Vito et al. |
| 4,781,179 A | | 11/1988 | Colbert |
| 4,817,588 A | | 4/1989 | Bledsoe |
| 4,834,078 A | * | 5/1989 | Biedermann ................. 602/27 |
| 4,953,543 A | | 9/1990 | Grim et al. |
| 5,014,690 A | * | 5/1991 | Hepburn ...................... 602/27 |
| 5,025,782 A | | 6/1991 | Salerno |
| 5,052,379 A | * | 10/1991 | Airy et al. ................... 602/16 |
| 5,230,681 A | * | 7/1993 | Hannum ..................... 482/121 |
| 5,242,378 A | | 9/1993 | Baker |
| 5,387,185 A | | 2/1995 | Johnson, Jr. et al. |
| D357,744 S | | 4/1995 | Cadoret |
| 5,490,831 A | | 2/1996 | Myers et al. |
| 5,571,078 A | * | 11/1996 | Malewicz .................... 602/27 |
| 5,782,785 A | | 7/1998 | Herzberg |
| 6,010,474 A | | 1/2000 | Wycoki |
| 6,039,707 A | | 3/2000 | Crawford et al. |
| 6,129,690 A | | 10/2000 | Hamlin et al. |

* cited by examiner

Primary Examiner—Denise M. Pothier
(74) Attorney, Agent, or Firm—Meroni & Meroni, P.C.; Charles F. Meroni, Jr.; Paul D. Pressley

(57) ABSTRACT

The improved longitudinal support structure is used in combination with a leg brace that provides support to a wearer's leg. The improved longitudinal support structure for longitudinally supporting the leg brace provides a pivot post attached to the outer lower portion of the leg brace. A support member extends from the outer lower portion of the leg brace. The support member has apertures through it to provide longitudinal adjustment and is rotatably connected to the pivot post through one of the apertures so that an end can rotate about the pivot post. A stop post limits the rotation of the support member to a predetermined range. A rigid cross member attached to the end of the support member positioned adjacent the wearer's ankle rests atop the wearer's foot and is shaped to accept the wearer's ankle. Means for securing the rigid cross member about the wearer's ankle is provided.

12 Claims, 3 Drawing Sheets

LEG BRACE SUPPORT STRUCTURE

BACKGROUND OF THE INVENTION

1. Field of the Invention

The present invention generally relates to leg braces and knee braces. More specifically, the present invention relates to an improved support structure for leg and knee braces.

2. Description of the Prior Art

Leg and knee braces as used in this field generally consist of a pair of rigid brace structures disposed on either side of the leg having an upper support strut connected to a lower support strut by a hinge structure situated adjacent the knee that allows the wearer to bend the knee while wearing the brace. In certain applications, the hinge structure comprises internal mechanical stops that limit the movement of the hinge structure and in turn limiting the movement of the knee. The hinge structures of this type are used when movement of the knee through a certain angle may cause damage to the knee. The rigid brace structures are usually held in place against the wearer's leg by a sleeve that fits over the thigh, knee, and calf and secured in place by adjustable straps. There are many different types of leg braces in the prior art. U.S. Pat. No. 4,781,179 issued to Colbert and U.S. Pat. No. 5,025,782 issued to Salerno are representative of many of the leg braces in the prior art, with the lower support struts terminating at the midpoint of the calf. Other leg braces, such as U.S. Pat. No. 4,817,588 issued to Bledsoe and U.S. Pat. No. 4,953,543 issued to Grim et al., have lower support struts that are adjustable to allow the wearer to make the lower support struts longer so that the brace is adjustable to the length of the wearer's leg. Leg and knee braces of this type all inherently have the similar problem of sliding down the leg as the leg is moved due to the rotation of the knee and the movement of the leg's muscles. The Grim et al. patent attempts to address this problem by providing a support collar to grip the wearer's leg just above the ankle. However, leg braces of this type still tend to slide down the wearer's leg upon movement of the leg muscles, knee, and ankle.

Another category of leg and knee braces generally consists of braces that are longitudinally supported about the leg by the shoe of the wearer. U.S. Pat. No. 5,490,831 issued to Myers et al and U.S. Patent No. 3,844,279 issued to Konvalin are generally representative of leg braces that attach to the heel of the wearer's shoe. These braces aid the rehabilitation of damaged leg muscles, or help the wearer who is paralyzed or suffered a stroke to walk. However, these leg braces require the leg brace wearer to wear a shoe that is capable of receiving the leg brace attachment in order to provide the longitudinal support of the leg brace.

Another category of leg and knee brace generally consists of braces that are longitudinally supported about the leg by providing a stirrup like structure that is fixed out the heel or foot of the wearer. U.S. Pat. No. 4,688,559 issued to Vito et al. and U.S. Pat. No. 5,242,378 issued to Baker are representative of these types of braces. These leg braces address the problem of the leg brace sliding down the wearer's leg during use by providing a stirrup like structure that is connected to the calf support members, thus preventing longitudinal movement of the leg brace. However, these braces are generally designed to immobilize the leg and are generally utilized under different circumstances than that of a wearer who can move the leg through a certain range of rotation without further injury to the knee.

Therefore, there exists a need for an improved leg brace that does not impair or require the use of a shoe in preventing the leg brace from sliding down the wearer's leg during use.

SUMMARY OF THE INVENTION

Accordingly, it is an object of the claimed invention to provide an improved Leg Brace Support Structure that provides longitudinal support to a leg or knee brace to prevent the brace from moving out of place during movement of the wearer's leg.

It is a further objective of the claimed invention to provide an improved Leg Brace Support Structure that can be made part of the leg brace to facilitate ease of putting on and taking off the Leg Brace Support Structure.

It is a further objective of the claimed invention to provide an improved Leg Brace Support Structure that is adjustable to accommodate the difference in length from one wearer's leg to another wearer's leg.

It is yet a further objective of the claimed invention to provide an improved Leg Brace Support Structure that allows the leg brace wearer to wear the leg brace more loosely while still maintaining the relationship between the rigid support structures of the leg brace with the wearer's thigh, knee, calf, and ankle.

For many different reasons people are fitted with leg braces to protect the leg from injury, prevent the leg from being injured further, or assist the healing process of the wearer's leg. A common problem with wearing a leg brace is the propensity of the leg brace to move out of place and slide down the leg during movement of the leg. The improved leg brace support structure prevents the leg brace from sliding down the leg of the wearer by providing a longitudinal leg brace support structure that rests atop the wearer's foot.

The longitudinal support structure is used in combination with an orthopedic leg brace. The combination comprises an inner rigid support structure on the interior side of a wearer's leg, the inner rigid support structure having an upper and lower portion. An outer rigid support structure is disposed on the exterior side of the wearer's leg, the outer rigid support structure having an upper and lower portion. At least one pivot post is fixedly attached to and extends perpendicularly from the lower portion of the outer rigid support structure. At least one elongated longitudinal support member extending substantially parallel to the wearer's leg from the lower portion of the outer rigid support structure, the elongated longitudinal support member having a plurality of apertures through and along the length of the elongated longitudinal support member to provide longitudinal adjustment of the longitudinal support structure, the elongated longitudinal support member rotatably connected to the pivot post through an aperture of the elongated longitudinal support member so that an end of the elongated longitudinal support member can rotate about the pivot post in an arc adjacent and substantially perpendicular to the axis of rotation of the wearer's ankle. At least one stop post attached to the lower portion of the outer rigid support structure, the stop post positioned to limit the rotation of the elongated support member to a predetermined range of rotation. At least one rigid cross member adjustably attached perpendicularly to the end of the elongated longitudinal support member so that the rigid cross member is positioned adjacent to the axis of rotation of the wearer's ankle, the rigid cross member shaped to accept and padded to protect the wearer's ankle. Means for securing the rigid cross member about the wearer's ankle.

Other advantages and aspects of the present invention will become apparent upon reading the following detailed description of the invention.

DETAILED DESCRIPTION OF THE PREFERRED EMBODIMENT

Figure 1:
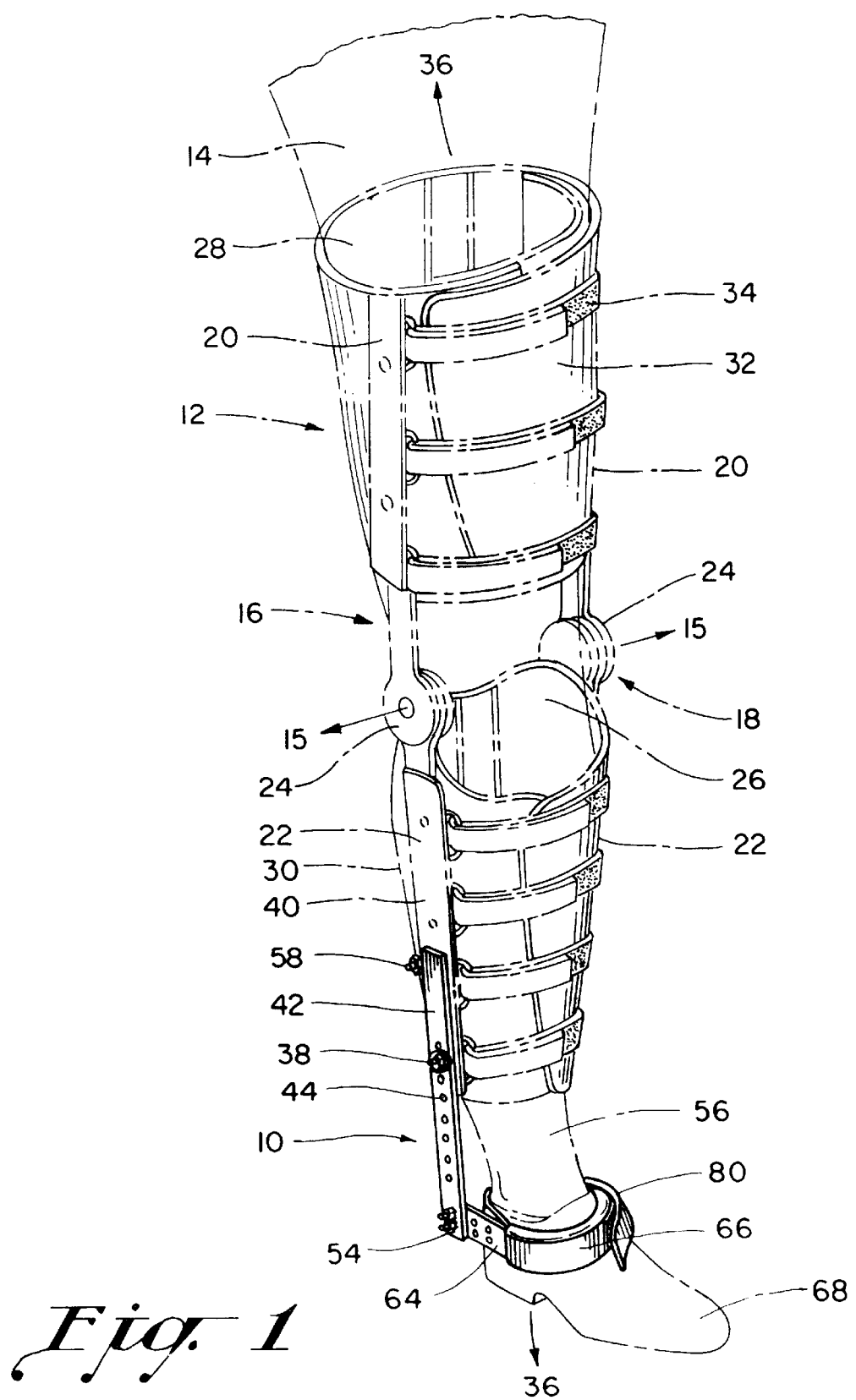
FIG. 1—Illustrates the improved leg brace support structure mounted to a leg brace as it is worn.
Figures 2, 3:
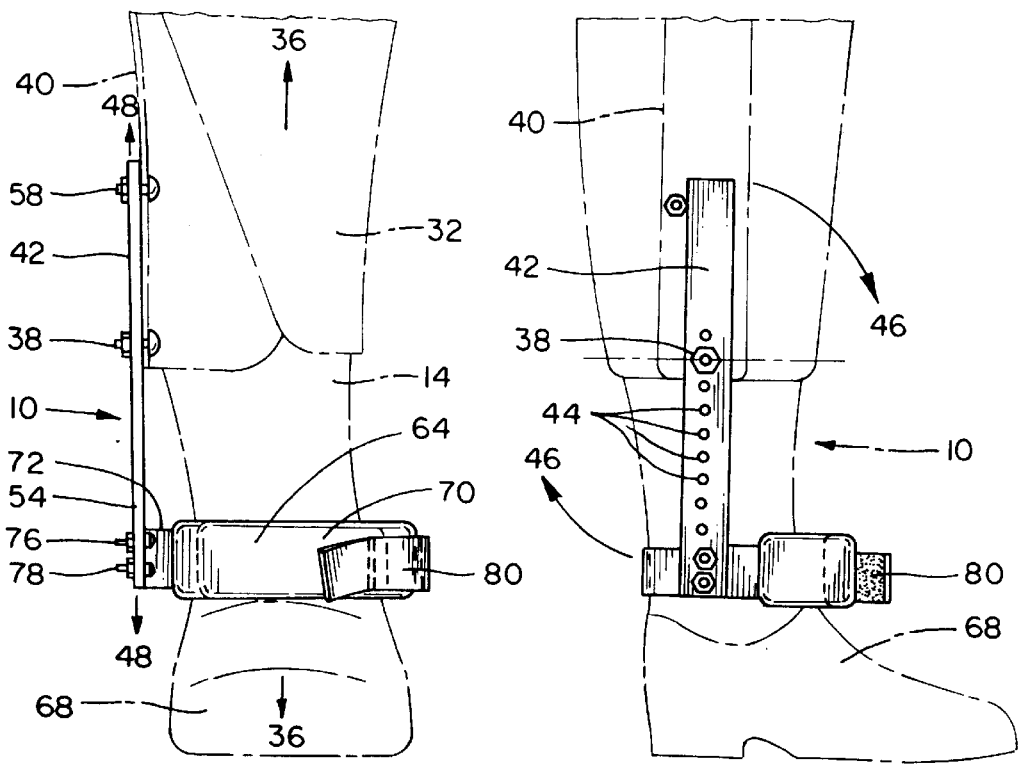
FIG. 2—Front view of the improved leg brace support structure.
FIG. 3—Side view of the improved leg brace support structure.
Figure 4:
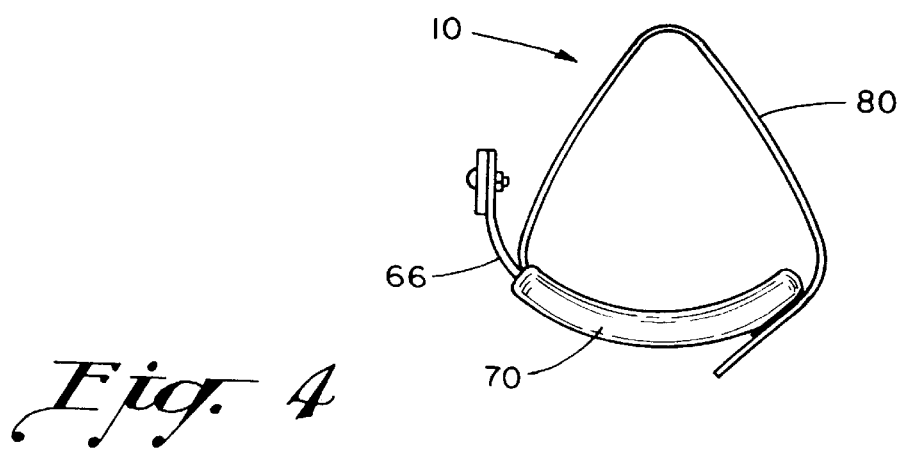
FIG. 4—Top view of the improved leg brace support structure.

While this invention is susceptible of embodiments in many different forms, there is shown in the drawings and will herein be described in detail a preferred embodiment of the invention. The present disclosure is to be considered as an exemplification of the principles of the invention and is not intended to limit the broad aspect of the invention to the embodiment illustrated.

FIG. 1 shows a person wearing a preferred embodiment of the improved longitudinal support structure 10. The leg brace 12 supports the wearer's leg 14 laterally 15 by providing support structure 16, 18 disposed on either side of the leg. The inner 18 and outer 16 support structures generally consist of an upper support strut 20 connected to a lower support strut 22 by a hinge structure 24 located adjacent the wearer's knee 26. The hinge structure 24 commonly have internal mechanical stops within the hinge structure 24 to limit the angle of rotation of the hinge structure 24, in turn limiting the range of angular movement of the wearer's knee 26. This use of the leg brace 12 helps a leg brace wearer that may sustain knee damage by rotating the knee through a certain angle by preventing the harmful rotation of the knee through the predetermined point. The upper support struts 20 are situated adjacent the wearer's thigh 28, and the lower support struts 22 are situated adjacent the wearer's calf 30. The inner 18 and outer 16 support structures are typically held in place against the leg 14 by a sleeve 32 that is placed over the leg 14 of the wearer. The leg brace 12 is then tightened against the wearer's leg 14 by straps or laces 34. The rigidity of the inner 18 and outer 16 support structures provide an increased amount of lateral support 15 to the wearer's knee 26 as the leg brace 12 is tightened against the wearer's leg 14 by preventing the wearer's femur and tibia from moving laterally 15 in relation to one another. This condition usually takes place when the wearer has damaged tendons, ligaments, and/or missing or damaged cartilage in the knee.

As a person wearing a leg brace 12 walks, the flexion and extension of the muscles in the leg 14 cause the tightened sleeve 32 around the leg 14 to loosen from the movement of the muscles. As the sleeve 32 loosens, the inner 18 and outer 16 support structures of the leg brace 12 tend to move out of place as the leg brace 12 slides down the wearer's leg 14 due to the lack of longitudinal support for the leg brace 12. As the inner 18 and outer 16 support structures of the leg brace 12 move out of place, the amount of lateral support 15 they provide to the wearer's leg 14 decreases, thus reducing the effectiveness of the leg brace 12. When the relationship between the leg brace hinges and the wearer's knee is lost, the leg brace may put an extra load on the wearer's knee. Thus it is desirable to maintain the relationship between the leg brace hinges and the wearer's knee.

The improved leg brace support structure 10 as shown in FIGS. 2–5 supports the leg brace 12 along the longitudinal axis 36 of the wearer's leg 14 by preventing the leg brace 12 from sliding down the wearer's leg 14. The longitudinal support provided by the improved leg brace support structure 10 increases the effectiveness of the leg brace 12 by maintaining the relationship between the wearer's leg 14 and the inner 18 and outer 16 support structures of the leg brace 12. This allows the wearer of the leg brace 12 with the improved leg brace support structure 10 to move more freely without having to frequently readjust and reposition the leg brace 12.

Figure 5:
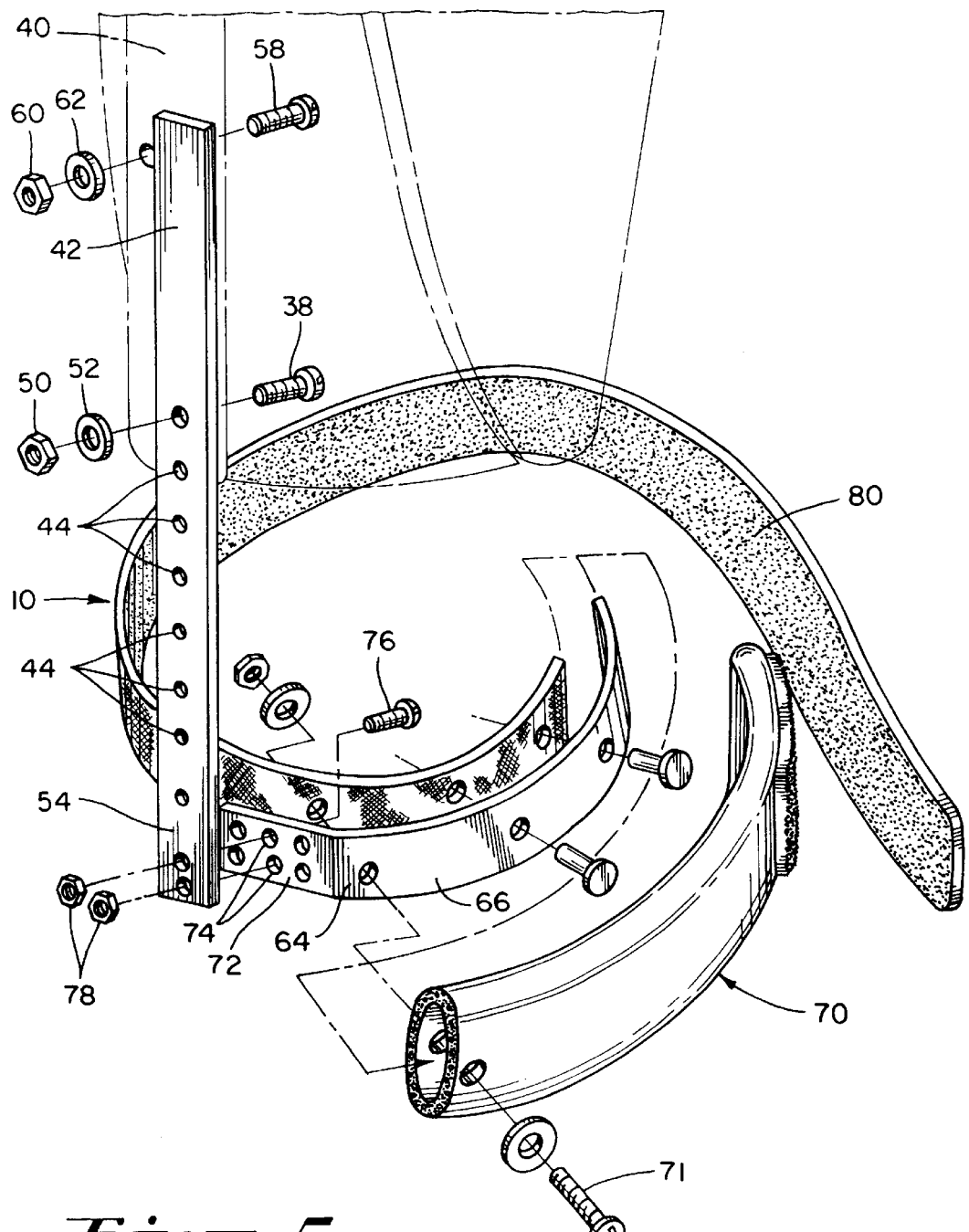
FIG. 5—Exploded view of the improved leg brace support structure.

The improved leg brace support structure 10 consists of a pivot post 38 fixedly attached to and extending perpendicularly from the outer lower support strut 40 of the leg brace 12 adjacent the calf 30. The pivot post 38 is attached to the outer lower support strut 40 through a hole that is made in the outer lower support strut 40. The preferred embodiment uses a steel 10–32×⅝" slotted pan head screw for the pivot post as shown in FIG. 5. However, the use of other more cost effective means of constructing the pivot post is contemplated.

A longitudinal support member 42 having a plurality of apertures 44 along its length is connected to the pivot post 38 through one of the apertures 44. The apertures are sized so that the longitudinal support member 42 can pivot 46 about the pivot post 38 in a plane parallel 48 to the longitudinal axis of the leg 36. See FIG. 2. The longitudinal support member 42 is held in place laterally 15 by an elastic stop nut 50 and washer 52 that are threaded onto and placed over the threads of the pivot post 38. The apertures 44 along the length of the longitudinal support member 42 allow it to be adjusted along the longitudinal axis 36 in relation to the outer lower support strut 40 of the leg brace 12 so that a first end of the longitudinal support member 54 may be positioned adjacent the wearer's ankle 56. When the longitudinal support member 42 is laterally 15 secured in place on the pivot post 38, the longitudinal support member 42 is substantially parallel with the longitudinal axis 36 of the wearer's leg 14. In the preferred embodiment, the longitudinal support member 42 is made of approximately ⅛" thick aluminum, has a length of approximately 7" and is approximately 1" wide. The apertures 44 along the length of the longitudinal support member 42 are spaced at intervals of approximately ⁵⁄₁₆" on center and are approximately ³⁄₁₆" in diameter. See FIG. 5.

A stop post 58 is fixedly attached to and extending perpendicularly from the outer lower support strut 40 of the leg brace 12 located in relationship to the pivot post 38 allowing the stop post 58 to prevent rotation of the longitudinal support member 42 through a predetermined point. In the preferred embodiment, the stop post 58 prevents the longitudinal support 42 member from rotating counterclockwise through a point that is perpendicular with the longitudinal axis of the wearer's leg. See FIG. 3. The stop post 58 is attached to the outer lower support strut through a hole that is made in the outer lower support strut. The preferred embodiment uses a steel 10–32×⅝" slotted pan head screw for the stop post as shown in FIG. 5. The stop post 58 is held in place by the stop post nut 60 and the stop post washer 62.

The rigid cross member 64, has a generally C shaped portion 66 to accept the leg brace wearer's ankle 56, rests atop the wearer's foot 68 to give the leg brace 12 longitudinal 36 support. See FIGS. 4 and 5. In the preferred embodiment, the C shaped portion 66 of the rigid cross member 64 has a radius of approximately 2" and is made of approximately ⅛" thick aluminum that is approximately 1" wide. The rigid cross member 64 is padded 70 to protect the leg brace wearer's ankle 56 and foot 68 from the rigid cross member 64. The padding is secured, as shown in FIG. 5, by a fastener 71, but it is contemplated to be secured by other similar means as well.

The outer end 72 of the rigid cross member 64 is connected to the longitudinal support member 42 through a plurality of apertures 74 that allow adjustment of the rigid cross member 64 in relation to the wearer's ankle 56. Spacers (not shown) may also be used to adjust the rigid cross member 64 laterally 15 to fit the wearer's ankle 56. The preferred embodiment uses two steel 10–32×½" slotted pan head screws 76 and nuts 78 to attach the rigid cross member 64 to the longitudinal support member 42. The rigid cross member 64 is secured to the leg brace wearer's ankle 56 by a flexible and adjustable strap structure 80 such as a belt or VELCRO. The adjustable strap structure 80 keeps the rigid cross member 64 secured around the leg brace wearer's ankle 56.

The improved leg brace support structure 10 supports the leg brace 12 longitudinally 36 by the rigid cross member 64 resting on the top of the leg brace wearer's foot 68. Since the longitudinal support member 42 is attached to both the rigid cross member 64 and the outer lower support strut 22 of the leg brace 12, the leg brace 12 can not move down the leg 14 due to the top of the wearer's foot 68 holding the rigid cross member 64 in place. As the top of the wearer's foot 68 holds the rigid cross member 64 in place, the improved leg brace support structure 10 hold the leg brace 12 in place, thus maintaining the relationship between the leg brace wearer's knee 26 and the leg brace hinges 24. The improved leg brace support structure 10 provides the advantage of being able to wear the leg brace 12 loosely tightened about the wearer's leg 14 while still preventing the leg brace 12 from slipping down the wearer's leg 14, thus allowing greater comfort and circulation in the wearer's leg 14.

The pivot feature of the support structure 10 allow the support structure 10 to move with the wearer's leg 14 independent from the movement of the leg brace 12. This feature prevents the support structure 10 from placing a load or apply pressure to the wearer's ankle 56 and prevents the flexible and adjustable strap structure 80 from injuring the wearer's Achilles tendon. The independent movement of the support structure 10 allows the wearer to walk with the support structure 10 and leg brace 12 in a natural fashion. In addition, if the wearer happens to make a sudden movement that may put a sudden load on the support structure 10, such as miss stepping or falling, the support structure 10 will move with the wearer's leg 14.

As various possible embodiments may be made in the above invention for use for different purposes and as various changes might be made in the embodiments and methods above set forth, it is understood that all of the above matters here set forth or shown in the accompanying drawings are to be interpreted as illustrative and not in a limiting sense.

I claim:

1. In combination, an orthopedic leg brace and a longitudinal support structure, the orthopedic leg brace comprising:
   an upper support strut;
   a lower support strut;
   a knee hinge connecting the upper support strut and the lower support strut;
   at least one pivot post fixedly attached to and extending perpendicularly from the lower strut;
   at least one elongated longitudinal support member extending substantially parallel to a wearer's leg from the lower strut during use, the elongated longitudinal support member having a plurality of apertures through and along the length of the elongated longitudinal support member to provide longitudinal adjustment of the longitudinal support structure, the elongated longitudinal support member rotatably connected to the pivot post through an aperture of the elongated longitudinal support member so that an end of the elongated longitudinal support member can rotate about the pivot post in an arc adjacent and substantially perpendicular to the axis of rotation of a wearer's ankle;
   at least one stop post attached to the lower strut, the stop post positioned to limit the rotation of the elongated support member to a predetermined range of rotation;
   at least one rigid cross member adjustably attached perpendicularly to the end of the elongated longitudinal support member so that the rigid cross member is positioned adjacent to the axis of rotation of a wearer's ankle, the rigid cross member shaped to accept and padded to protect a wearer's ankle; and
   means for securing the rigid cross member about the wearer's ankle.

2. The leg brace of claim 1 wherein the plurality of apertures through the elongated longitudinal support member are spaced 5/16" apart.

3. The leg brace of claim 2 wherein the stop post limits the rotation of the elongated longitudinal support member to a range of rotation in a clockwise direction.

4. The leg brace of claim 3 wherein the rigid cross member is C shaped.

5. The leg brace of claim 4 wherein the means for securing the rigid cross member about a wearer's ankle is an adjustable hook and loop strap assembly.

6. The leg brace of claim 5 wherein the rigid cross member has a plurality of apertures through the rigid cross member at one end so that the rigid cross member can be adjusted to fit a wearer's ankle.

7. In an orthopedic leg brace having an upper support strut and a lower support strut connected to the upper support strut by a knee hinge, the improvement comprising:
   at least one pivot post fixedly attached to and extending perpendicularly from the lower support strut;
   at least one elongated longitudinal support member extending substantially parallel to a wearer's leg during use from a lower portion of the lower support strut, the elongated longitudinal support member having a plurality of apertures through and along the length of the elongated longitudinal support member to provide longitudinal adjustment of the longitudinal support structure, the elongated longitudinal support member rotatably connected to the pivot post through an aperture of the elongated longitudinal support member so that an end of the elongated longitudinal support member can rotate about the pivot post in an arc adjacent and substantially perpendicular to the axis of rotation of the wearer's ankle;
   at least one stop post attached to the lower support strut, the stop post positioned to limit the rotation of the elongated support member to a predetermined range of rotation;
   at least one rigid cross member, the rigid cross member adjustably attached perpendicularly to the end of the elongated longitudinal support member so that the rigid cross member is positioned adjacent to the axis of rotation of a wearer's ankle, the rigid cross member shaped to accept and padded to protect a wearer's ankle; and
   means for securing the rigid cross member about the wearer's ankle.

8. The leg brace of claim 7 wherein the plurality of apertures through the elongated longitudinal support member are spaced 5/16" apart.

9. The leg brace of claim 8 wherein the stop post limits the rotation of the elongated longitudinal support member to a range of rotation in a clockwise direction longitudinally parallel to the wearer's leg.

10. The leg brace of claim 9 wherein the rigid cross member is C shaped.

11. The leg brace of claim 10 wherein the means for securing the rigid cross member about the wearer's ankle is an adjustable hook and loop strap assembly.

12. The leg brace of claim 11 wherein the rigid cross member has a plurality of apertures through the rigid cross member at one end so that the rigid cross member can be adjusted to fit the wearer's ankle.

* * * * *